(12) United States Patent
Tezuka

(10) Patent No.: US 6,251,085 B1
(45) Date of Patent: Jun. 26, 2001

(54) MEDICAL GUIDEWIRE

(75) Inventor: Toshiaki Tezuka, Kanagawa-ken (JP)

(73) Assignee: Olympus Optical Co., Ltd., Tokyo (JP)

( * ) Notice: Subject to any disclaimer, the term of this patent is extended or adjusted under 35 U.S.C. 154(b) by 0 days.

(21) Appl. No.: 09/103,368

(22) Filed: Jun. 23, 1998

(30) Foreign Application Priority Data

Jul. 4, 1997 (JP) .................................................. 9-179972

(51) Int. Cl.$^7$ ...................................................... A61B 5/00
(52) U.S. Cl. ......................... 600/585; 600/433; 604/95; 604/280
(58) Field of Search ................................... 600/585, 433, 600/434; 604/95, 96, 280, 281, 282

(56) References Cited

U.S. PATENT DOCUMENTS

| | | |
|---|---|---|
| 4,579,127 | 4/1986 | Haacke . |
| 5,111,829 | 5/1992 | Alvarez de Toledo . |
| 5,251,640 * | 10/1993 | Osborne ................................. 600/585 |
| 5,344,315 * | 9/1994 | Hanson ................................... 433/20 |
| 5,769,796 * | 6/1999 | Palermo et al. ........................ 600/585 |
| 5,827,201 * | 10/1998 | Samson et al. ........................ 600/585 |
| 5,910,364 * | 6/1999 | Miyata et al. ......................... 600/585 |
| 6,019,736 * | 2/2000 | Avellanet et al. ..................... 600/585 |

FOREIGN PATENT DOCUMENTS

| | | |
|---|---|---|
| 33 27 779 A1 | 2/1985 | (DE) . |
| 0 826 389 A2 | 3/1998 | (EP) . |
| 61-7735 | 3/1986 | (JP) . |
| 62-231675 | 10/1987 | (JP) . |
| 2-180277 | 7/1990 | (JP) . |
| 2-40992 | 10/1990 | (JP) . |
| WO 98/16274 | 4/1998 | (WO) . |

OTHER PUBLICATIONS

German Literature: Verlag Knaur, München: Grimm–Rapunzel, p. 103.

* cited by examiner

Primary Examiner—Cary O'Connor
Assistant Examiner—Pamela L. Wingood
(74) Attorney, Agent, or Firm—Frishauf, Holtz, Goodman, Langer & Chick, P.C.

(57) ABSTRACT

The present invention provides a guidewire having a reduced diameter, which ensures rigidity and excellent guidance ability in spite of its reduced diameter, and which achieves an excellent sliding ability and insertion/pulling-out ability with respect to a catheter or the like. The guidewire has an inner core formed of a single wire having an uneven surface on its outer circumferential surface, a high-polymer coating which densely covers the outer circumferential surface of the inner core, and an uneven surface formed on the outer circumferential surface of the high-polymer coating by an influence from the uneven surface on the outer circumferential surface of the inner core.

14 Claims, 1 Drawing Sheet

MEDICAL GUIDEWIRE

BACKGROUND OF THE INVENTION

The present invention relates to a guidewire for guiding a medical device having a hollow structure such as a catheter or the like, which is introduced into a human body directly or through an endoscope in a medical treatment or inspection.

In recent years, medical treatments have come to introduce positively a technique which makes less incision damages to a human body. Specifically, in place of an incision operation, such as abdominal section, thoracotomy or the like, which provides a heavy physical burden to a patient, an inspection and a treatment carried out by inserting various catheters into a human cavity have come to be used. In case of practicing such a technique, it is general that a guidewire is inserted through a catheter which is to be inserted into a human body and a device such as the catheter or the like is guided to an aimed body cavity portion along the guidewire. Many guidewires of this kind are used in an inspection or a treatment on a stomach, duodenum, bile duct, cholecyst, liver, pancreatic duct, pancreas, or the like, as a digestive organ.

Conventional guidewires for digestive organs, used with the technique of such a low incision damage, are suggested in Japanese Patent Application KOKAI Publication No. 2-180277 and U.S. Pat. No. 5,111,829, for example. Each of these guidewires has an inner core made of a superelastic metal and an X-ray contrast portion provided at the top end, and the entire of the inner core and the X-ray contrast portion is coated with a synthetic resin. The coating has a substantially uniform outer diameter and has an outer circumferential surface which is shaped into a smooth and even cylindrical surface without roughness.

However, in the guidewires described above, the outer circumferential surface of synthetic resin coating the inner core has a smooth cylindrical shape without roughness. Therefore, in case of actually guiding a catheter by the guidewire described above, the inner circumferential surface of the catheter is closely contacted on and intensively sticks to the smooth and even outer circumferential surface of the guidewire. The friction resistance when the guidewire slides is large and makes worce an operability in inserting and/or pulling out a catheter.

In this respect, Japanese Utility Model Application KOKOKU Publication No. 2-40992, Japanese Patent Application KOKAI Publication No. 62-231675, Japanese Utility Model KOKOKU Publication No. 61-7735, and U.S. Pat. No. 4,579,127 have proposed guidewires each of which has an outer circumferential surface formed in an uneven shape in order to decrease the friction resistance to a catheter or the like.

In the guidewire suggested in Japanese Utility Model Application KOKOKU Publication No. 2-40992, a tube-like member freely engaged on the inner core is formed of a net-like member or the outer circumferential surface of the tube-like member is processed by a lacquer ware with a flecked effect, so that the outer circumferential surface of the tube-like member is formed to have an uneven surface.

In the guidewire according to Japanese Patent Application KOKAI Publication No. 62-231675, a thin wire-like inner core is coated with a relatively thick coating layer, and the outer circumferential surface portion of the coating layer is formed to be uneven.

In the guidewire according to Japanese Utility Model Application KOKOKU Publication No. 61-7735, a relatively thin coating film is applied to the outer circumference of the coil-like spring composing the guidewire, such that the coating film has an uneven shape.

U.S. Pat. No. 4,579,127 suggests a catheter and a probe-mandrel, which are comprised of a wire core and an external wire wound like a coil on the wire core, and a thin resin-made coating layer of a uniform thickness is formed on the semicircular circumferential surface.

The guidewire according to Japanese Utility Model Application KOKOKU Publication No. 2-40992 is made of a tube-like member freely engaged on an inner core and has a drawback that the structure is complicated and thick. Although its thickness, its rigidity is rather low, and further, the guidewire lacks a force transmission ability when it is twisted.

In the guidewire according to Japanese Patent Application KOKAI Publication No. 62-231675, its narrow wire-like inner core is coated with a relatively thick coating layer, so that the guidewire tends to be thickened with ease. The rigidity of the guidewire is rather low in spite of its thickness. Further, the guidewire lacks a force transmission ability when it is twisted. In the guidewire according to Japanese Utility Model Application KOKOKU Publication No. 61-7735, it comprises a coil-like spring as a core member, so that the guidewire lacks rigidity and a force transmission ability when it is twisted. Further and the follow-up ability of its top end portion is low.

Further, the mandrel according to U.S. Pat. No. 4,579,127 has a structure in which an external wire is wound like a coil on the wire core, so that the guidewire has low rigidity although it has flexibility, and the guidewire lacks force transmission ability when it is twisted. In this structure, the function of guiding a catheter or the like easily tends to be affected. Also, the entire guidewire must be thickened to improve the rigidity and the transmission ability. However, such a guidewire is not preferable as a guidewire.

BRIEF SUMMARY OF THE INVENTION

The present invention has been made in view of the problems described above and has an object of providing a guidewire having a reduced diameter, which ensures rigidity and excellent guidance ability in spite of its reduced diameter, and which achieves an excellent slide ability and insertion ability with respect to a catheter or the like.

According to the present invention, there is provided a guidewire for using with a medical device having a hollow structure, comprising: an inner core formed of one of a strand formed of a plurality of wire elements without a core member and a single wire, the inner core having an outer circumferential surface having at least a part formed of an uneven surface; and a high-polymer coating having an outer circumferential surface and covering the outer circumferential surface of the inner core, the outer circumferential surface of the high-polymer coating having an uneven surface formed by the uneven surface of the outer circumferential surface of the inner core.

According to the guidewire, an uneven surface is formed on the outer circumferential surface of the coating by an influence from the unevenness of the outer circumferential surface of the inner core, and as a result, the contact portion of the guidewire with respect to a catheter or an endoscope channel is dispersed into several points. Since the contact area is thus reduced, the guidewire is prevented from sticking to the catheter or the endoscope channel. The uneven surface of the outer circumferential surface of the inner core forms the outer circumferential surface of the coating into an uneven surface, so that the shape of the unevenness of the outer circumferential surface of the coating can be controlled finely and easily by appropriately selecting the shape of the unevenness of the outer circumferential surface of the inner core.

Therefore, the inner core of the guidewire according to the present invention is formed of a single wire or a strand without a core member. The inner core is coated with a coating and the uneven shape formed on the outer circumference of the inner core appears on the outer circumference of the coating. Accordingly, regardless of a coating having an uneven outer circumferential surface, the thickness of the coating is thinned in comparison with the thickness of the inner core, and the guidewire is very thin and attains high rigidity. At the same time, the ability of transmitting a force required for operation is excellent when the guidewire is twisted, and the follow-up ability of the distal end of the guidewire is also excellent.

As has been described above, according to the present invention, the contact portion in contact with a catheter, an endoscope channel, or the like is dispersed into several points, by the uneven shape of the outer circumferential surface of the coating caused by the uneven shape of the outer circumferential surface of the inner core of the guide wire. In this manner, the contact area of the contact points is decreased to prevent the guidewire from sticking to the catheter or the endoscope channel. Therefore, the guidewire can be smoothly slid by a slight force, so that the guidewire can be smoothly inserted or pulled out.

In addition, since the uneven shape of the outer circumferential surface of the coating is shaped along the uneven shape of the outer circumferential surface of the inner core, the outer circumferential surface of the coating can be easily controlled by appropriately selecting the outer circumferential shape of the inner core. Accordingly, the shape of the outer circumferential surface of the fine coating can be easily created.

Further, since the uneven shape formed on the outer circumferential surface of the inner core is arranged so as to appear on the outer circumferential surface of the coating, the thickness of the coating can be reduced in comparison with the thickness of the inner core even though the outer circumferential surface of the coating has an uneven shape. Accordingly, it is possible to provide a guidewire which is very thin and has excellent rigidity. When the guidewire is twisted, the ability of transmitting a force, which is necessary for operation, is excellent, and the distal end portion of the guidewire has an excellent follow-up ability.

Preferably, the inner core has an elongated and thin main body portion at least a part of which is made of metal having a superelastic characteristic, a distal end portion extending from the main body portion and having a smaller diameter than the main body portion, and a high X-ray contrast portion provided at the distal end portion.

In addition, the outer circumferential surface of the inner core preferably has at least one of a spiral groove and a spiral projection, extending along a longitudinal axis of the inner core.

At least a part of the inner core preferably has a superelastic characteristic.

Further, the high X-ray contrast portion contains any metal selected from a group of gold, silver, platinum, tungsten, bismuth oxide, palladium, and tantalum, as a main component.

The high X-ray contrast portion preferably includes one of a coil-like shape and a pipe-like shape.

At least a part of the high-polymer coating is preferably made of a material selected from a group of fluorine-based resin, polyethylene, polyester, polypropylene, polyamide, polyurethane, polystyrene, elastomer thereof, polyvinyl chloride, and silicon rubber.

The high-polymer coating preferably has a lubrication layer on the outer circumferential surface, and the lubrication layer preferably includes a lubrication material applied onto a portion of the outer circumferential surface of the high-polymer coating.

Further, the guidewire can preferably be used for digestive organs.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments give below, serve to explain the principles of the invention.

DETAILED DESCRIPTION OF THE INVENTION

[First Embodiment]

Figure 1A:
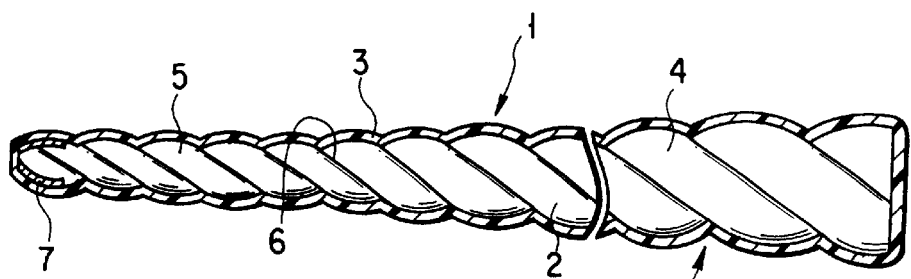
FIGS. 1A and 1B are respectively longitudinal and transversal cross-sectional views showing a medical guidewire according to a first embodiment of the present invention.
Figure 1B:
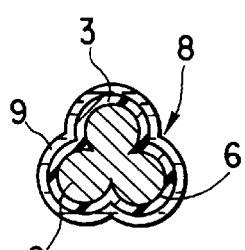

FIGS. 1A and 1B show a medical guidewire according to a first embodiment of the present invention.

(Structure)

The guidewire 1 integrally consists of an inner core 2 formed of a single wire having an elasticity, and a coating 3 made of synthetic resin (of high-polymer or high-molecular weight compound) which covers substantially the entire of the inner core 2. The guidewire 1 according to the present embodiment has, for example, an outer diameter of about 0.2 to 0.8 mm and an overall length of about 2 to 3 meter, and is formed as a guidewire for a digestive organ, which is useful when used together with a duodenum drainage tube or an endoscope, for example.

The inner core 2 is made of an integral member comprising of a main body portion 4 which is relatively thick and rigid, and a distal end portion 5 which has a smaller diameter than the main body portion 4 and is tapered to be gradually thinned. The inner core 2 is made of an elastic material, e.g., pseudoelastic metal such as SUS or the like, or is made of superelastic metal or the like containing nickel and titanium as its main components. Superelastic alloy containing nickel and titanium as main components is suitable for the inner core 2. In addition, only the portion in the side of the top end, which requires a sufficient elasticity, may be formed of superelastic metal.

A groove 6 or a projection which extends spirally along the axial direction is formed on the outer circumference of the inner core 2. Specifically, like stranded wires as shown in a second embodiment described later, the groove or projection is formed in the same uneven shape of the outer circumferential surface as will be obtained where three wires are stranded together. Naturally, the groove 6 or the projection may have a different shape other than a spiral shape. Also, the groove 6 or the projection may have an appropriate cross-sectional shape other than the shape defined by curves as shown in FIG. 1B.

A high X-ray contrast portion 7 is provided at the front end portion of the distal end portion 5 of the inner core 2. The high X-ray contrast portion 7 is coated with a coating 3. The high X-ray contrast portion 7 is, for example, a thin wire wound like a coil or a film-like portion having a cylindrical shape. The material of the portion 7 may be gold, silver, platinum, tungsten, bismuth oxide, palladium, tantalum, or alloy containing any of them as its main component, or may preferably be platinum.

The outer circumferential surface of the inner core 2 is coated densely with a coating 3 having a uniform thickness, and the coating 3 is coated to be fitted tightly on the outer circumferential surface of the inner core 2, and an undulatory uneven surface 8 which corresponds to the shape of the outer circumferential surface of the inner core 2 defines the outer circumferential surface of the coating 3. The uneven portion 8 formed on the outer circumferential surface of the coating 3 may be provided entirely over the coating 3 or may be provided only at the portion where a high resistance will be generated when inserting and pulling out the guidewire.

The material of the coating 3 may preferably be synthetic resin or particularly be fluorine-based resin such as PTFE or the like. However, another resin material (e.g., polyethylene, polyester, polypropylene, polyamide, polyurethane, polystyrene, elastomer thereof, or elastomer containing polyvinyl chloride, silicon rubber, or the like) may be used.

The coating 3 on the outer circumferential surface of the inner core 2 may be applied by dipping or application, or may be formed by thermally shrinking the tube made of thermally shrinkable resin and fitted on the inner core 2. The shape of the uneven surface 8 appearing on the outer circumferential surface of the coating 3 (e.g., the depth and/or pitch of its groove(s)) can be easily controlled by the shape of the outer circumferential surface of the inner core 2.

In the present embodiment, a thin lubrication layer 9 is provided on the entire or a part of the outer circumferential surface of the coating 3. The lubrication layer 9 may be formed of a lubrication material such as a silicon oil or the like applied on the surface, or a hydrophilic material (which is preferably polyvinyl alcohol, polyvinyl pyrolidone, or the like) upon necessity.

(Operation and advantages)

For example, when a catheter is actually guided by the guide wire 1, the contact area in contact with inner surfaces of the catheter or an endoscope channel is reduced with the uneven surface 8 on the outer circumferential surface of a coating 3 coated on the outer circumferential surface of the inner core 2, to prevent the guidewire from sticking to the inner surface of the catheter or endoscope channel. Both the guidewire and the catheter are smoothly slid with a slight force to facilitate guidance of the catheter and insertion into the endoscope channel. The surface of the coating of the present invention facilitates the insertion and withdrawal of the guide wire 1 easier as compared with a conventional guidewire having a even surface of synthetic resin.

Specifically, the outer circumferential surface of the guidewire 1 according to the present invention has an uneven shape, so that the contact portion in contact with the inner surface of the catheter, the endoscope channel, or the like is dispersed to several points on the uneven shape of the outer circumferential surface of the guidewire when the guidewire 1 is inserted into a catheter, a digestive organ, or an endoscope channel. Therefore, the guidewire 1 slides more excellently than the conventional guidewire having a smooth and even surface and the guidewire 1 can be smoothly inserted and pulled out.

Also, in the guidewire 1 according to the present embodiment, a coating 3 is coated on an inner core 2 composed of a single wire, and the shape of a spiral groove 6 or a projection formed on the outer circumferential surface of the inner core 2 is arranged so as to appear on the outer circumferential surface of the coating 3. Therefore, in spite of a coating 3 which forms a fine uneven surface 8 on the outer circumferential surface, the coating 3 can be thinned in comparison with the thickness of the inner core 2 of the guidewire 1. As a result, it is possible to provide a guidewire 1 having an excellent recovery ability and high rigidity even if the guidewire is very thin. In addition, since the inner core 2 comprises a single wire, the guidewire has an excellent transmission ability when the guidewire is twisted, and the distal end portion of the guidewire also has an excellent follow-up ability.

Further, the guidewire 1 slides in a catheter, an endoscope channel, or the like and can be smoothly inserted or pulled out. Therefore, the guidewire 1 can be used for a catheter having an inner diameter much closer to the outer diameter of the guidewire 1.

The shape of the uneven surface 8 formed on the outer circumferential surface of the guidewire 1 can be easily controlled by appropriately selecting the shape of the outer circumferential surface of the inner core 2, so that even a fine outer circumferential shape can be easily formed.

In the present embodiment, the guidewire 1 according to the present embodiment can be used in a situation in which it is not possible to insert and pull out a conventional guidewire, by providing a lubricity for the outer circumferential surface of the coating of the guidewire 1.

[Second Embodiment]

Figure 2A:
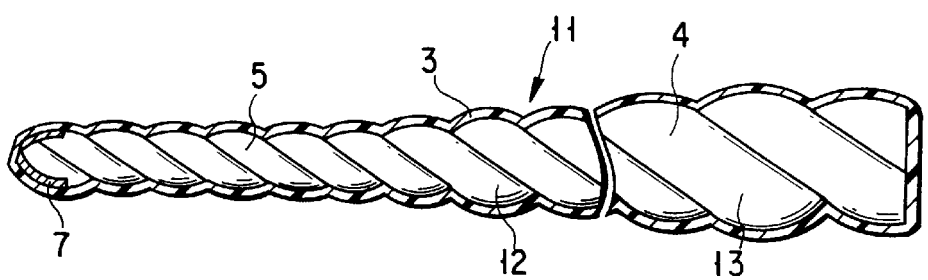
FIGS. 2A and 2B are longitudinal and transversal cross-sectional views showing a medical guidewire according to a second embodiment of the present invention.
Figure 2B:
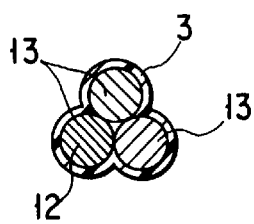

FIGS. 2A and 2B show a medical guidewire according to a second embodiment of the present invention.

(Structure)

The guidewire 11 according to the second embodiment has an inner core 12 composed of a strand without a core member, and the strand has three wires or wire elements stranded together. Each of wires 13 of the inner core 12 is made of an elastic material, e.g., pseudoelastic metal such as SUS or the like, or superelastic metal or the like containing nickel and titanium as its main components. Also, superelastic metal containing nickel and titanium as its main components is preferably used for the wires 13. Of course, at least the portions of the wires 13 at the distal end portions that require a sufficient elasticity may be made of superelastic metal. The other components of the structure are the same as those of the guidewire 1 according to the first embodiment described above.

(Operation and Advantages)

In the guidewire 11 according to the second embodiment, the inner core 12 is formed of the strand without a core member, so that the inner core 12 can be formed to be very thin and it is possible to provide a guidewire 11 having an excellent flexibility, an excellent kink-resistance, an excellent recover ability, and a high rigidity. In addition, since the inner core 12 is formed of a strand without a core member, the transmission ability, which is required during operation, when the guidewire 11 is twisted is more excellent than in the case in which the coiled wire is used for the inner core. Accordingly, the follow-up ability of the distal end portion of the guidewire is improved. In addition, even if the wires 13 of the inner core 12 are made of SUS or the like, it is possible to obtain substantially the same torque transmission ability as in the case where the inner core 12 made of single wire 13 is made of superelastic metal.

In addition, it is possible to achieve the same operation and advantages as those obtained in the second embodiment described above.

The wires 13 of the inner core 12 according to the present embodiment may be constructed by combining wires 13 made of different materials, having different diameters, or having different cross-sectional shapes. Also, the guidewire according to the present invention includes a medical guidewire used for circulatory organs other than digestive organs.

Additional advantages and modifications will readily occurs to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A guidewire for use with a medical device having a hollow structure, comprising:
   an inner core selected from the group consisting of
     (a) a strand formed of a plurality of wire elements without a core member, and
     (b) a single wire; the inner core having an outer circumferentially uneven surface having; and
   a high-polymer coating having an outer circumferential surface and covering the outer circumferential surface of the inner core, the outer circumferential surface of the high-polymer coating having an uneven surface formed by the uneven surface of the outer circumferential surface of the inner core the uneven surface dispersing contact points for the guidewire to provide excellent slideability with respect to the medical device.

2. A guidewire according to claim 1, wherein the inner core has an elongated thin main body portion at least a part of which is made of metal having a superelastic characteristic, a distal end portion extending from the main body portion and having a diameter smaller than that of the main body portion, and a high X-ray contrast portion provided at the distal end portion.

3. A guidewire according to claim 1, wherein the outer circumferential surface of the inner core has at least one selected from the group consisting of a spiral groove and a spiral projection, extending along a longitudinal axis of the inner core to form the uneven surface.

4. A guidewire according to claim 1, wherein at least a part of the inner core has a superelastic characteristic.

5. A guidewire according to claim 2, wherein the high X-ray contrast portion contains any metal selected from the group consisting of gold, silver, platinum, tungsten, bismuth oxide, palladium, and tantalum, as a main component.

6. A guidewire according to claim 2, wherein the high X-ray contrast portion includes one selected from the group consisting of a coil-like shape and a pipe-like shape.

7. A guidewire according to claim 1, wherein at least a part of the high-polymer coating is made of a material selected from the group consisting of fluorine-based resin, polyethylene, polyester, polypropylene, polyamide, polyurethane, polystyrene, elastomer thereof, polyvinyl chloride, and silicon rubber.

8. A guidewire according to claim 1, wherein the high-polymer coating has a lubrication layer on the outer circumferential surface.

9. A guidewire according to claim 8, wherein the lubrication layer includes a lubrication material applied onto a portion of the outer circumferential surface of the high-polymer coating.

10. A guidewire according to claim 1, wherein the guidewire is applicable for digestive organs.

11. A guidewire for use with a medical device having a hollow structure, comprising:
    an inner core selected from the group consisting of
      (a) a strand formed of a plurality of wire elements without a core member, and
      (b) a single wire; the inner core having an outer circumferentially uneven surface; and
    a high-polymer coating having an outer circumferential surface and covering the outer circumferential surface of the inner core, the outer circumferential surface of the high-polymer coating having an uneven surface formed by the uneven surface of the outer circumferential surface of the inner core; and
    wherein at least a part of the inner core has a superelastic characteristic.

12. A guidewire according to claim 11, wherein the said at least a part of the inner core with a superelastic characteristic has an elongated thin main body portion at least a part of which is made of metal having a superelastic characteristic, the elongated thin metal body portion having a distal end portion extending from the main body portion and having a diameter smaller than that of the main body portion, and a high X-ray contrast portion provided at the distal end portion.

13. A guidewire according to claim 12, wherein the high X-ray contrast portion contains a metal selected from the group consisting of gold, silver, platinum, tungsten, bismuth oxide, palladium, and tantalum, as a main component.

14. A guidewire according to claim 12, wherein the high X-ray contrast portion includes one selected from the group consisting of a coil-like shape and a pipe-like shape.

* * * * *

UNITED STATES PATENT AND TRADEMARK OFFICE
CERTIFICATE OF CORRECTION

| | |
|---|---|
| PATENT NO. | : 6,251,085 B1 |
| APPLICATION NO. | : 09/103368 |
| DATED | : June 26, 2001 |
| INVENTOR(S) | : Toshiaki Tezuka |

It is certified that error appears in the above-identified patent and that said Letters Patent is hereby corrected as shown below:

Title Page, under "References Cited, U.S. Patent Documents", after
"5, 769,796" line 5 delete "6/1999" and replace with - -6/1998 - -.

Column 7, (claim 1), lines 33 to 37 delete

"an inner core selected from the group consisting of
    (a) a strand formed of a plurality of wire elements
without a core member, and
    (b) a single wire; the inner core having an outer circumferentially uneven
surface; and"

and replace with:

--an inner core formed of a single wire; the inner core having an outer
  circumferentially uneven surface; and - -

Column 8, (claim 11), lines 27-31 delete
"an inner core selected from the group consisting of
    (a) a strand formed of a plurality of wire elements without a core member, and
    (b) a single wire; the inner core having an outer circumferentially uneven
surface; and"

and replace with:

--an inner core formed of a single wire; the inner core having an outer
  circumferentially uneven surface; and - -

Signed and Sealed this

Twenty-second Day of August, 2006

JON W. DUDAS
*Director of the United States Patent and Trademark Office*